(12) United States Patent
Marchitto et al.

(10) Patent No.: US 6,492,634 B2
(45) Date of Patent: Dec. 10, 2002

(54) OPTICAL MONITOR FOR SUDDEN INFANT DEATH SYNDROME

(75) Inventors: Kevin S. Marchitto, Mt. Eliza (AU); Stephen T. Flock, Mt. Eliza (AU)

(73) Assignee: Rocky Mountain Biosystems, Inc., Golden, CO (US)

(*) Notice: Subject to any disclaimer, the term of this patent is extended or adjusted under 35 U.S.C. 154(b) by 0 days.

(21) Appl. No.: 09/847,449

(22) Filed: May 2, 2001

(65) Prior Publication Data

US 2002/0030154 A1 Mar. 14, 2002

Related U.S. Application Data

(60) Provisional application No. 60/201,510, filed on May 3, 2000.

(51) Int. Cl.[7] ............................... G01J 3/50; H01J 5/16
(52) U.S. Cl. ..................................... 250/221; 250/336.1
(58) Field of Search ............................. 250/221, 336.1, 250/338.1, 339.02, 339.1, 339.14, 340, 341.8; 128/664, 716, 719

(56) References Cited

U.S. PATENT DOCUMENTS

| 4,350,166 | A | 9/1982 | Mobarry | 128/664 |
| 5,309,921 | A | 5/1994 | Kisner | 128/719 |
| 5,386,831 | A | 2/1995 | Gluck | 128/664 |
| 5,800,360 | A | 9/1998 | Kisner | 600/532 |
| 6,062,216 | A | 5/2000 | Corn | 128/204.23 |

Primary Examiner—Hung Xuan Dang
(74) Attorney, Agent, or Firm—Benjamin Aaron Adler

(57) ABSTRACT

The present invention provides devices and/or methods of monitoring extremely small movements associated with infant breathing and heart rate, therefore monitoring sudden infant death syndrome (SIDS). Provided is a system for monitoring movement of an infant, comprising: a light source which produces radiant energy; an optical device; and an imaging device. Further provided is a method of monitoring movement of an infant, comprising the steps of: producing radiant energy by a light source; coupling said radiant energy into an optical device so as to create a matrix of images; projecting said images into a field of interest; and detecting movement of said infant using an imaging device.

20 Claims, 2 Drawing Sheets

OPTICAL MONITOR FOR SUDDEN INFANT DEATH SYNDROME

CROSS-REFERENCE TO RELATED APPLICATION

This non-provisional patent application claims benefit of provisional patent application U.S. Ser. No. 60/201,510, filed May 3, 2000, now abandoned.

BACKGROUND OF THE INVENTION

1. Field of the Invention

The present invention relates generally to the field of medical devices. More specifically, the present invention relates to an optical monitor for sudden infant death syndrome.

2. Description of the Related Art

Sudden Infant Death Syndrome (SIDS) is the sudden and unexpected death of an apparently healthy infant, whose death remains unexplained after further medical investigation such as an autopsy. Sudden Infant Death Syndrome is neither a disease, nor can it be a diagnosis for a living baby [1]. SIDS occurs at a rate of approximately 2 per 1,000 live births in the United States and occurs most often (90%) in under six months of age; of these, 18% were preterm infants [2].

One of the events that occurs during Sudden Infant Death Syndrome is a period of apnea (stoppage of breathing) during which it may be possible that the infant may be resuscitated. However, most Sudden Infant Death Syndrome events occur at night when the infant's caregiver is asleep. Since Sudden Infant Death Syndrome is not normally associated with verbal distress, few infants get a chance to be resuscitated.

Fortunately, the number of Sudden Infant Death Syndrome deaths has decreased at a steady rate. The Sudden Infant Death Syndrome rate for 1995 was 0.87 deaths per 1,000 live births [3]. It is notable that more children die of Sudden Infant Death Syndrome in a year than all children who die of cancer, heart disease, pneumonia, child abuse, AIDS, cystic fibrosis, and muscular dystrophy combined [4]. According to Dr. J. D. DeCristofaro of the University Medical Center Stony Brook, NY, (SIDS Network Internet Website, December 1998), the sibling of a SIDS baby will be on a monitor past the age of the Sudden Infant Death Syndrome death, but a minimum of 6 months. Typically, the parents are not ready to give up the monitor at such time and often continue monitoring for up to a year.

Clearly, some sort of continuous monitoring of the infant for the presence or absence of breathing would be of value. Such a monitor could sound an alarm that would awaken the care-giver when breathing stopped, and further possibly acoustically stimulate the infant thereby stimulating the breathing reflex. In clinics, there exist a multitude of instruments, such as pneumotachometers or plesthymographs that, with little modification, could be used for this purpose. However, these devices are quite expensive and are not practical for use at home, particularly in infants with no history of being at risk for SIDS.

Transthoracic electrical impedance monitors are by far the most frequently applied, have the widest availability in the United States, and are generally efficacious in identifying and alarming on apnea events. With these instruments, however, are some situations where "breaths" are detected during true apneas (false negative) and other cases where apneas are indicated while is breathing (false positive). The former is also a significant concern with impedance monitors thus limiting their usefulness.

Any monitor that accurately reflects the predisposing condition must consistently be alert and understandable to the care giver. In other words, the monitor must be efficacious in recognizing apnea and capable of triggering an alarm for prolonged apnea. Short periods of apnea (15 seconds) may not be fatal to an infant, but prolonged apnea (20 seconds) is abnormal [2]. In addition, the monitor must be capable of recognizing its own internal operating functions to assure proper and uninterrupted operation. Ideally, it must be noninvasive and easy to use and understand. Other desirable features would be the capability of collecting and archiving patterns surrounding significant events for later analysis. These could include estimation of tidal volume, the identification of heart rate patterns and variability as well as cardiac arrhythmias.

Therefore, the prior art is deficient in the lack of effective apparatus and/or means for monitoring sudden infant death syndrome. The present invention fulfills this long-standing need and desire in the art.

SUMMARY OF THE INVENTION

The present invention is directed to devices and/or methods of monitoring sudden infant death syndrome (SIDS).

In one embodiment of the present invention, there is provided a system consisting of a sensitive optical rangefinder which senses the movement of a spot of light, projected onto the sleeping infant.

In another embodiment of the present invention, there is provided a method and/or system of using a laser, the radiant output of which is passed through a diffractive optic whereby a matrix of spots is projected into the crib. The movement of the infant is detectable by monitoring the movement of the image of the spots on a charge-coupled device (CCD). Alternatively, a light source such as a superluminescent infrared light-emitting diode (LED) can be used rather than a laser.

In another embodiment of the present invention, there is provided a system for monitoring movement of an infant, comprising: a light source which produces radiant energy; an optical device; and an imaging device.

In another embodiment of the present invention, there is provided a method of monitoring movement of an infant, comprising the steps of: producing radiant energy by a light source; coupling said radiant energy into an optical device so as to create a matrix of images; projecting said images into a field of interest; and detecting movement of said infant using an imaging device.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

DETAILED DESCRIPTION OF THE INVENTION

The present invention provides a device which has the sensitivity to continuously detect extremely small movements associated with infant breathing and heart rate. The present device provides several advantages, including being small, inexpensive, and non-contacting.

In one embodiment of the present invention, there is provided a system comprising of a sensitive optical rangefinder which senses the movement of a spot of light, projected onto the sleeping infant. By doing so, sudden infant death syndrome can be monitored. In the present system, the signals are continually monitored and analyzed for false-positive events.

In another embodiment of the present invention, there is provided a method and/or system of using a laser, the radiant output of which is passed through a diffractive optic whereby a matrix of spots is projected into the crib. The movement of the infant is detectable by monitoring the movement of the image of the spots on a charge-coupled device (CCD). Alternatively, a light source can be used rather than a laser. For example, a superluminescent infrared light-emitting diode (LED), which illuminates the crib and sleeping infant with invisible radiant energy and a sensitive photo-detector can be used, wherein any lack of movement of the infant translates into a static reflected infrared signal. In the present method/system, the signals are continually monitored and analyzed for false-positive events.

Fuzzy-logic is incorporated into the software in the microprocessor that controls the instrument and analyzes the data. The fuzzy-logic "learns" the typical movement pattern of the infant, thus providing a pattern with which spurious signals can be rejected. If an apnea event is detected, a signal can be transmitted to a receiver (alarm) positioned in proximity to the care-provider thus alerting them to the fact. The output of the device can be connected to a computer or telephone line where it is electronically transmitted to a monitoring company.

Optionally, the optical device could be configured with a sensitive acoustic sensor. Certain movement of the infant would create some acoustic signal, beyond the signal associated with the rush or air through the oral or nasal cavity. The problem with stand-alone acoustic sensors is that they are sensitive to extraneous environmental noises and so are problematic in that they produce many false-negative signals. However, the combination of a n acoustic monitor with an optical movement monitor, whereby the two signals could be collected simultaneously and compared, would allow for the rejection of false-negative signals and/or false positives.

The following examples are given for the purpose of illustrating various embodiments of the invention and are not meant to limit the present invention in any fashion.

EXAMPLE 1

Figure 1:
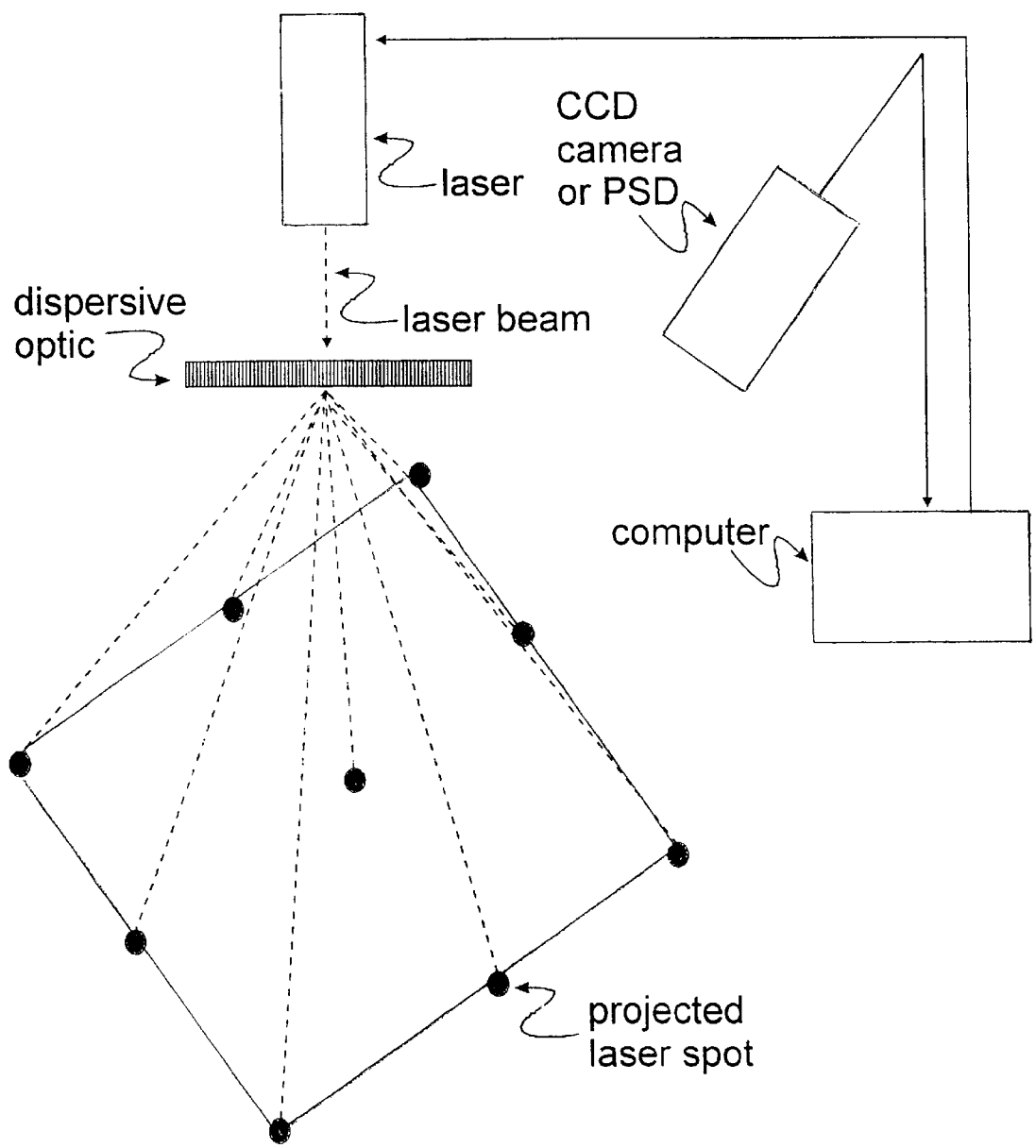
FIG. 1 is a diagram of the arrangement whereby movements are measured by monitoring the changes in position and intensity of an array of projected circles with a position-sensitive-detector (PSD) or charge-coupled-device (CCD) camera.
Figure 2:
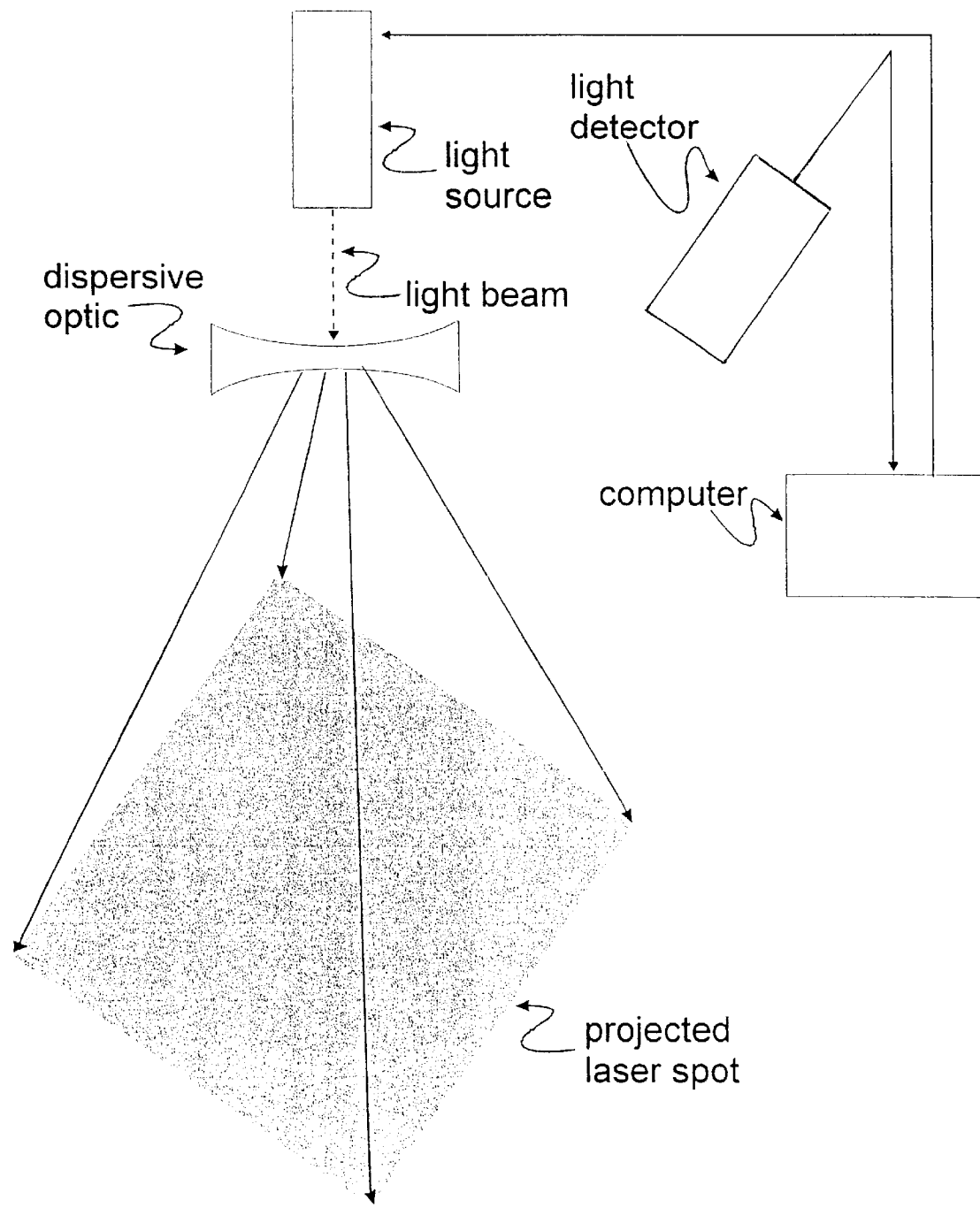
FIG. 2 is a diagram of the arrangement whereby movements are measured by the change in reflected light intensity as measured by a photosensitive detector.

Various Means of Monitoring Infant Movement The method and device invented for measuring the external movement associated with cardio-respiratory function has several different embodiments. FIG. 1 shows one arrangement. In this case, radiant energy (visible or near-infrared) is produced by a light source (which is optimally a superluminescent infrared-light-emitting diode, but optionally can be a diode laser or incandescent bulb). The radiant energy is coupled into a diffractive optic (or other passive or active optical device) which serves to create a matrix of images which is then projected into the field of interrogation, in part or its entirety. This field, for example, could be a baby's crib. Examples of other systems that would be useful are an optoacoustic deflector (see FIG. 2), diffraction grating, or array of apertures behind a rotating aperture. The images that make up the projected matrix may be made up various patterns, for example, circles or x's. The projected matrix is then imaged by a device which is sensitive to any movement or intensity change in the images.

In this example, a charge-coupled-device (CCD) camera could image the entire field. The output of the camera would then b e monitored by a computer whereupon the x,y position (in terms of pixels on the CCD) and the intensity of each spot is determined. It is possible to continually monitor the position and intensity of the images on the CCD with appropriate software. If desirable, given the optical transfer properties of the imaging system, it is possible to calibrate movement on the CCD(in pixels) with actual movement (in centimeters) on the baby.

In any case, the software program has a criteria in terms of average or typical spot movement (in pixels) or intensity changes (digitized electron number) for which it associates normal movement associated with normal respiration. At the beginning of a monitoring session, the software can "learn" the typical normal movements of the subject using fuzzy logic. This can then be used to reduce or eliminate false positives and false negatives during the subsequent monitoring. A memory could be incorporated into the hardware so that a record of the monitoring session could be downloaded at a later time if necessary.

The output of the device may be monitored b y transmitting a radio signal to a receiver either locally or at a remote location (typically near the care-giver). In an alarm situation, the receiver can emit a tone and flash a light thereby alerting the care-giver to the fact that an abnormal cardiac and/or respiration event is taking place in the baby's crib. Alternatively, the output of the unit can be monitored by a company over a telephone connection or over a connection to the internet through a computer and modem or such. The attraction in the latter case is that an inexpensive video monitor which images the infant may also be included in the package such that a health care professional could closely observe any infant who is presumably experiencing an apnea event, and contact the caregiver quickly by phone if the warrants are needed.

The following references were cited herein.
1. American SIDS Institute. Internet Website, December 1998.
2. NIH Consensus Statement Online Sep. 29–Oct. 1 1986 [cited Dec. 8 1998]; 6 (6):1–10.
3. CDC and National Center for Health Statistics. Internet Website, December 1998.
4. SIDS Alliance. Internet Website, December 1998.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A sudden infant death syndrome monitoring system, comprising:
   a light source which produces radiant energy;
   an optical device that creates and projects a matrix of images; and
   an imaging device that detects movement of said images so as to monitor sudden infant death syndrome.

2. The system of claim 1, further comprising:
   a means for continually monitoring said signals.

3. The system of claim 2, further comprising:
   software capable of analyzing data.

4. The system of claim 2, further comprising:
   a means for transmitting a signal to a receiver when an apnea event is detected.

5. The system of claim 4, wherein said receiver is selected from the group consisting of an alarm, a computer and a telephone line.

6. The system of claim 1, wherein said radiant energy is selected from the group consisting of visible or near-infrared.

7. The system of claim 1, wherein said light source is selected from the group consisting of a laser, a superluminescent infrared-light-emitting diode, a diode laser and an incandescent bulb.

8. The system of claim 1, wherein said optical device is selected from the group consisting of a passive or active optical device.

9. The system of claim 1, wherein said optical device is a diffractive optic.

10. The system of claim 1, wherein said imaging device is a charge-coupled device.

11. The system of claim 1, wherein said light source is a superluminescent infrared-light-emitting diode and said imaging device is a sensitive photo-detector.

12. The system of clam 1, further comprising a sensitive acoustic sensor.

13. A method of monitoring movement of an infant, comprising the steps of:
    producing radiant energy by a light source;
    coupling said radiant energy into an optical device so as to create a matrix of images;
    projecting said images into a field of interest; and
    detecting movement of said infant using an imaging device.

14. The method of claim 13, wherein said radiant energy is selected from the group consisting of visible or near-infrared.

15. The method of claim 13, wherein said light source is selected from the group consisting of a laser, a superluminescent infrared-light-emitting diode, a diode laser and an incandescent bulb.

16. The method of claim 13, wherein said optical device is selected from the group consisting of a passive or active optical device.

17. The method of claim 13, wherein said optical device is a diffractive optic.

18. The method of claim 13, wherein said imaging device is a charge-coupled device.

19. The method of claim 13, wherein said light source is a superluminescent infrared-light-emitting diode and said imaging device is a sensitive photo-detector.

20. The method of clam 13, wherein said field is a crib.

* * * * *